United States Patent
Winsel et al.

[11] Patent Number: 6,045,938
[45] Date of Patent: Apr. 4, 2000

[54] LINEAR ELECTRO CHEMICAL CONDUCTOR ELEMENT, PROCESS FOR ITS MANUFACTURE AND APPARATUS FOR ITS USE

[76] Inventors: August Winsel, Fasanenstrasse 8A, D-65779 Kelkheim; Hans Sauer, Pflasterwiese 7, 65510 Idstein-Walsdorf, both of Germany

[21] Appl. No.: 09/088,992

[22] Filed: Jun. 2, 1998

[30] Foreign Application Priority Data

Jun. 8, 1997 [DE] Germany .................. 197 24 007

[51] Int. Cl.[7] .................................................. H01M 10/34
[52] U.S. Cl. .................................. 429/60; 429/90; 429/91; 429/225; 429/228; 204/433; 204/435; 204/279; 204/280; 204/265
[58] Field of Search ......................... 429/61, 90, 91, 429/225, 228; 204/433, 435, 280, 279, 265

[56] References Cited

U.S. PATENT DOCUMENTS

| | | | |
|---|---|---|---|
| 5,242,565 | 9/1993 | Winsell | 204/265 |
| 5,288,563 | 2/1994 | Saito et al. | 429/91 |
| 5,407,555 | 4/1995 | Winsell | 204/435 |

*Primary Examiner*—Bruce F. Bell
*Attorney, Agent, or Firm*—Schnader Harrison Segal & Lewis LLP; Gerard J. Weiser

[57] ABSTRACT

The invention pertains to linear electrochemical functional elements which consist of strip-shaped ion-exchange membranes (IEMs) and/or hydrogen-diffusion electrodes accessible at the ends which are enclosed on all sides in an insulating manner by a jacket of a solid material. The invention describes the structure, production and use of the functional elements in electrochemical measuring techniques.

9 Claims, 2 Drawing Sheets

LINEAR ELECTRO CHEMICAL CONDUCTOR ELEMENT, PROCESS FOR ITS MANUFACTURE AND APPARATUS FOR ITS USE

FIELD OF THE INVENTION

The subject of the present invention is linear electrochemical functional elements, processes for their production and measuring instruments using them.

BACKGROUND OF THE INVENTION

The primary field of application of the linear electrochemical functional element described in the following is electrochemical measurement techniques, especially with hydrogen electrodes. From DE-PS 41 12 784.6 and the corresponding international application PCT/EP 92/00597, a hydrogen rod electrode with integrated hydrogen source is known. In it a hydrogen evolution cell according to DE-PS 35 32 335 is used in order to supply a hydrogen-diffusion electrode with hydrogen. Two constructions are described there which differ with respect to the active measuring electrode. The essential elements of the design are described in FIGS. 1 and 2.

In FIG. 1 the hydrogen electrode (1) consists of a platinized platinum wire which is positioned in the opening of a hydrogen tube (3) tapering to a point and made of glass, Plexiglas or other material that is as impermeable to hydrogen as possible. The other end of the hydrogen tube is screwed, plugged or glued gas-tight into the actual gas cell container (7). This preferably cylindrical gas cell container (7) holds the hydrogen evolution cell (9) according to DE-PS 35 32 335. It contains zinc powder or zinc gel and caustic potash together with the so-called hydrogen evolution electrode. On the latter a PTFE-bound catalyst film is rolled into a metal net and carries on the side away from the zinc a laminated fine-pored PTFE foil. The zinc electrode and the hydrogen evolution electrode are located in a housing which is usually made up of two metal parts insulated from each other, one of which is connected to the zinc electrode, the other to the hydrogen evolution electrode in an electron-conducting manner. The housing part containing the hydrogen evolution electrode communicates via at least one boring with the interior of the gas tube (3). The boring can be sealed by a sticker which releases the hole during operation of the cell as a result of excess pressure. The sticker may consist of a metal foil such as copper according to DE application 195 07 658.3.

The gas cell container (7) is closed by the screwed-on or pushed-on lid (10) which may have several functions. Thus after closing, advisably by means of elastic spring elements (not shown), it exerts a pressure on the cell (9) so that the latter communicates by means of the ring-shaped gasket (8) through the aforementioned boring in the cell housing part with the gas tube (3). These spring elements may be the electronic contacts (12) and (13) which contact the two housing parts. The lid (10) also advisably carries a fixed or variable electrical resistance (11) in series with an on-off switch to which the contacts (12) and (13) are connected. This may be, for example, a potentiometer with an "off" position. Instead of a lid, this electrical switching and current-regulating circuit may also be connected to the gas cell container (7).

To avoid disturbances caused by foreign gases, the metal layer from the hydrogen electrode is guided, inside the hydrogen tube if possible or embedded in its jacket, to the gas cell container where it terminates in a contact screw (6) accessible from the outside or a single-pole plug socket.

Platinum electrodes are suitable especially for use in acid media, because they resist all oxidizing acids in them. In addition, however, many other metals of the 8th Group of the Periodic System of the Elements, their alloys or electron-conducting solid bodies metallized with them are suitable for use as long as they possess the catalytic capabilities for chemisorptive splitting of the hydrogen molecule. This is true, for example, for palladium and iridium but also for activated carbon which is catalyzed by these metals. In this case black, large-area coatings are characterized as especially effective. In alkaline and neutral solutions nickel is a highly effective hydrogen catalyst, especially in the form of Raney nickel. This is a powdered material which is obtained from a nickel/aluminuim alloy by extraction of the aluminum with a caustic alkali. Hydrogen electrode bodies can be produced from it by means of powder-metallurgical production processes. Such procedures are described in the book by E. Justi and A. Winsel, Fuel Cells, Steiner Verlag, Wiesbaden 1962 and the patents listed in it. Electrodes suitable for this purpose, however, are also produced from a catalyst powder by intensive mixing with PTFE powder in a very high speed knife mill and rolling the powder mixture out into a metal net. Such electrodes are also advisably coated on one side with a fine-pored hydrophobic PTFE film which faces the reacting gas and keeps the three-phase boundary electrode/electrolyte/gas stable. Such electrode structures are described in EP-PS 144 002 (1983). However, it may be advantageous to improve the storage capacity by using so-called hydride storage alloys in addition to the Raney nickel, DE-OS 37 02 138 (1987).

In FIG. 2 the hydrogen electrode (1) is such a gas diffusion electrode which is contacted with a metal ring (2) and which is affixed by the holding cap (4) to the tube (3). It may be used in any position in an electrochemical measuring cell. The coupling of the above-described hydrogen electrode with the measurement object in an electrochemical cell is determined by the geometric shape and the inflexible structure. However, it is desired to have a reference electrode which can be installed as closely as possible to the contact of an equipotential surface also in a narrowly constructed primary or battery cell. The solution of this problem is the subject of the present invention.

Definition: In a polyelectrolyte (PE) the one type of ion is macromolecular and tetravalent while the counterion consists of the usual highly mobile ions. Both types of ions are hydrated and participate in hydrogen exchange in osmotic competition with their surroundings. In ion exchangers (IEs) many such macromolecular ions are connected by covalent bonds to networks which are insoluble because of their size; therefore they consist of fixed ions and mobile counterions which dissociate away according to the law of mass action and which can be replaced by ions of the same sign. Only these mobile counterions may contribute to electrical transport; the nonmobile fixed ions do not contribute to the conductivity. There are anion exchangers (AIEs) with mobile anions as counterions and a polyvalent cationic solid, as well as cation exchangers (CIEs) with mobile cations as counterions and a polyvalent anionic solid. Ion-exchange membranes (IEMs) are homogeneously or nonhomogeneously constructed membrane bodies which, because of their exchange action, involve only the counterions in the mass transfer by electric current and electrodialysis.

Generally the ion exchanger excludes the penetration of ions of the same sign as that of the solid ions. In the case when ion exchangers and ion-exchange membranes are used in highly concentrated solutions, especially strong electrolytes, foreign ions of the same sign as the solid ions are carried into the solid body with the water of hydration, thereby contributing to the electrical current and electrodialytic mass transfer. However, even in such small three-dimensional elements of IEs and IEMs, the charge balance is always neutral when averaged over time. For extensive literature on IEs and IEMs refer to "Römpp Chemie Lexikon", vol. 3, published by Jurgen Falbe, Manfred Regitz (1995), Verlag G. Thieme, Stuttgart.

The swelling behavior of IEs and IEMs is determined by the water economy. It can be used to measure the concentration in aqueous solutions. A simple representation of the processes occurring here is given in the following article: A. Winsel "Concentration measurements with ion-exchange membranes", Chemie-Ing.-Techn. 44 (1972) 163–167.

If one conceives of an IE or an IEM enclosed in a solid and undeformable housing with walls which are permeable for water vapor but are impermeable for non-water molecules, then a hydrostatic pressure gradient is formed between the inner and outer space. This is equal to the osmotic pressure difference between the IE or IEM on the one hand and the surrounding solution on the other. If the osmotic pressure gradient is always directed in such a way that the enclosed IE can remove water from the environment, then the IE cannot change significantly in its ion concentration nor in its water content and other characteristics.

A large number of ion exchangers and ion-exchange membranes exists. Thus the polyvalent solid may be a strong acid radical $[-SO_3^-]_n$ or a weak acid radical $[-COO^-]_n$; but it may also be a strong $[-N(CH_3)^+]_n$ or weak base $[-N(CH_2)^+]_n$. In each case neutralized with the corresponding counterions, we are dealing with a large number of salts. They may dissociate according to the mass action laws valid in each case and conduct electric current. In suitable combination they are buffering substances which adjust a narrow pH value. In electrochemistry in recent decades the membrane invented by W. Grot and made of Nafion, a poly (perfluoroalkylene)sulfonic acid, has proven especially effective. Nafion® is a trademark of the Du Pont Co. The Nafion material is available as a powder or as a solution. Ion-exchange membranes of Nafion material are freely supporting or welded onto PTFE fabric. Membrane-like ion exchangers can be produced in various ways. According to our experience this is especially simple if the powdered initial material of an IE is mixed with PTFE powder in a high-speed knife mill (reactive mixing) and a skin is formed from the cotton-like material by rolling. This IEM skin in a broad range of compositions consists of a cohesive cold-welded ion-exchange skeleton in a netlike PTFE web. An electrolytic conducting structure is formed both with and without secondary thermal treatment within the IEM body despite the hydrophobic action of the PTFE as a result of swelling. By mixing in powdered buffering salts one can assure that the ion concentration as well as the pH will vary only slightly with the IEM in the application case.

By mixing in catalyst powders for the hydrogen reaction, biporous structures can be produced in which the IE skeleton forms the electrolyte and the catalyst skeleton the electron conductor. The gas in question may flow in the hydrophobic range of the PTFE structure. As catalyst powder, activated carbon especially is used alone or as a carrier for the mobile metal catalyst of platinum, palladium, nickel or other metals or alloys. However metallic catalysts may also be used as highly coarse powders such as the Raney metals. These are obtained as residual metals by dissolving an alloying component out of a powdered alloy.

SUMMARY OF THE INVENTION

The invention pertains to linear electrochemical functional elements which consist of strip-shaped ion-exchange membranes (IEMs) and/or hydrogen-diffusion electrodes accessible at the ends which are enclosed on all sides in an insulating manner by a jacket of a solid material. The invention describes the structure, production and use of the functional elements in electrochemical measuring techniques.

DETAILED DESCRIPTION OF THE INVENTION

Figure 1:
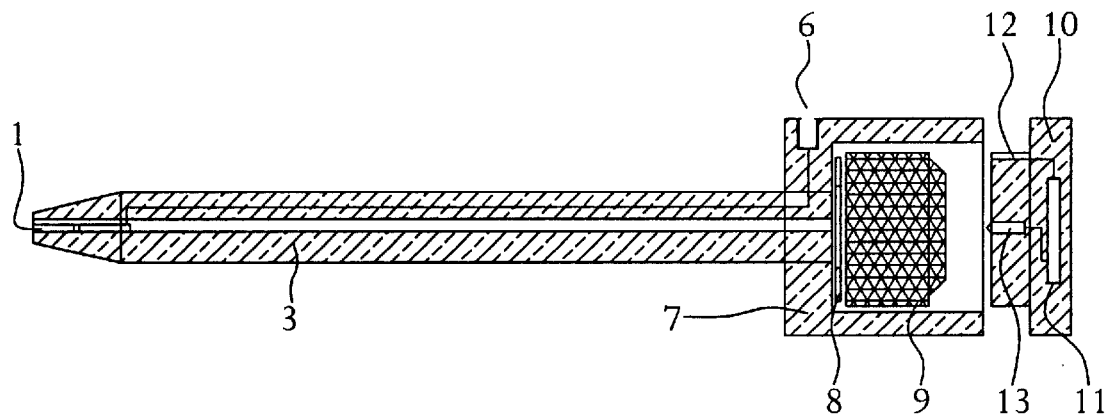
FIG. 1 is a schematic cross-sectional view of a hydrogen electrode of the prior art.

We have found that useful linear conductive structures can be produced from an ion-exchange membrane which are both shape-stable and also pH-stable. For this purpose a strip cut out of an IEM is placed in the fitting groove of a casting tool and embedded in a casting resin on all sides. In this way an electrolytic conductor of, e.g., 2 mm width and 1 mm thickness, is formed which is open at both ends and which may be used as an electrolyte key in electrochemical measurements. It is flexible and can be used, for example, in the set of plates of a starter battery. As a connection to a reference electrode (electrochemical key) in this way the polarization behavior of the two electrodes of the battery cell can be monitored exactly during the charging and discharging of the cell.

In order to obtain an especially stable linear conductor the IEM strip can also be inserted in a round or flat metal tube which has a passive surface. This is the case with titanium, for example, because titanium becomes coated with a non-conducting and insoluble film of $TiO_2$. Anodized aluminum also has the property of being passive to many solutions. To exclude reactions on the outer surface of the tube, it can be coated with an insulating layer of enamel or resin. For this purpose one may also use polymer heat-shrinkable tubing of polyethylene or polyvinyl fluoride which may still have a film of casting resin in the interior.

In many cases it is advantageous to insert the IEM strip with or without casting resin directly into heat-shrinkable tubing and to shrink it in a hot stream of air, at which time the casting resin is simultaneously cured. The heating can also be formed under a hot flatiron or in a hot roll in order to produce a linear ion conductor with an insulating jacket.

We have found that it is also possible to produce useful linear conducting structures from gas electrodes which are both stable in shape and stable in potential. For this purpose a strip is cut out of an electrode tape, placed in the fitting grove of a casting die and eebedded in casting resin on all sides. In this way an electronically conducting catalytically acting, electrolyte drawing strip of, e.g. 2 mm width and 1 mm thickness, which is open at both ends is formed. On one side it can be supplied with hydrogen and electrically contacted, while on the other side it can be immersed in the electrolyte of the measuring cell. The strip is flexible and may be used, for example, in the set of plates of a starter battery or in a fuel cell as a reference electrode. Thus the polarization behavior of the two electrodes can be monitored during a load on the measuring cell.

In order to obtain an especially stable linear structure the electrode strip can also be inserted in a flat metal tube which has a passive surface at the potential of the gas electrode. This is the case, for example, for hydrogen electrodes in the presence of copper and nickel and all noble metals. Titanium also which becomes coated with a nonconducting and insoluble film of $TiO_2$ may also be used. Anodized aluminum also has this property of being passive to many solutions. In order here also to exclude reactions on the outer surface of the tube it may be coated with an insulating enamel or resin. For this one may also use polymer heat-shrinkable tubing of polyethylene or polyvinyl fluoride. In many cases it is advantageous to place the electrode strip directly in the heat-shrinkable tubing and to shrink it in a stream of hot air or under a flatiron or in a hot roll in order to produce a linear gas electrode with an insulating coating.

For the version of a linear electrode strip described above, practically all structures of gas electrodes are suitable. They may consist only of a rolled skin. For this purpose catalyst powder and PTFE powder are mixed reactively and shaped in a roll. In addition the electrode, however, may also contain a metal net which improves the electrical conductivity in the direction of the strip. It may also contain a laminated-on PTFE foil in order to facilitate the longitudinal flow of the reaction gas. Of interest for the applications to be described in detail below are those linear structures in which IEM strips and gas electrode strips—by overlapping—form a half-cell. It is advantageous if the overlap zone is tightly welded by pressing or hot pressing. The hydrogen electrode then operates in an IE electrolyte which is specified by the nature and concentration of the ion exchanger and may be used as a standard. The individual linear functional elements and their coupling to the hydrogen rod electrode with integrated hydrogen source will now be described in some examples. For simplicity, in the examples, the other part of the gas tube together with the container will be regarded as a constant component for the gas evolution cell.

Figure 2:
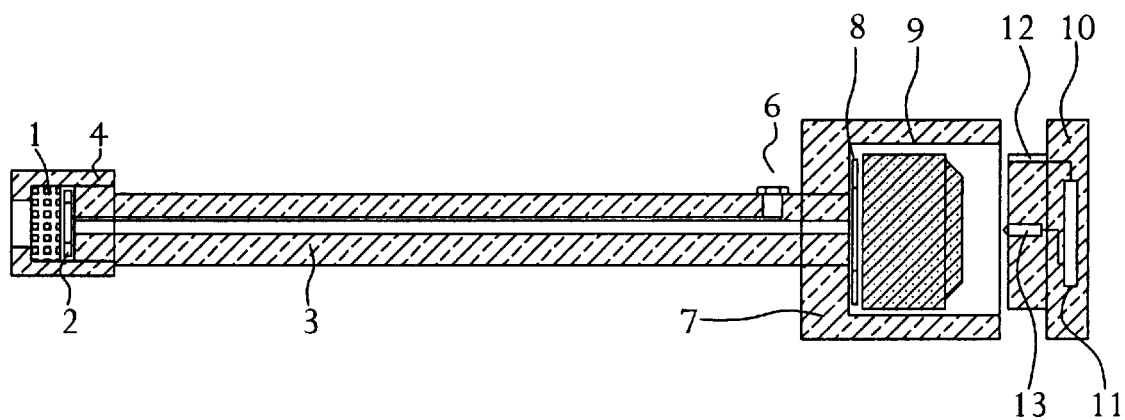
FIG. 2 is a schematic cross-sectional view of another hydrogen electrode of the prior art.
Figure 3:
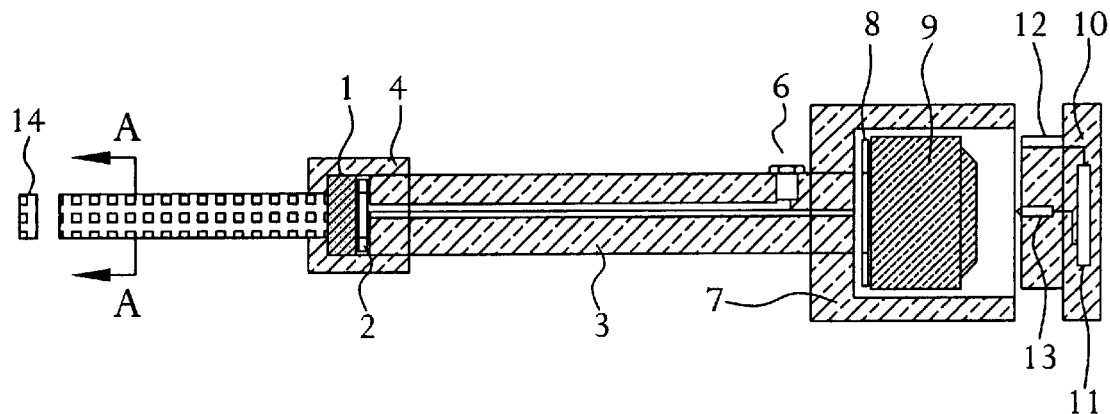
FIG. 3 is a schematic, cross-sectional view of a hydrogen electrode of the invention.

FIG. 3 shows how the hydrogen rod electrode shown in FIG. 2 can be provided with a tongue-like tip (14). The section A—A illustrates the strip-like character of the linear IEM element. It is inserted or glued in a closely fitting manner into the holding cap (4) and contacted electrolytically with the hydrogen electrode (1). The front end of the tongue scans the electrode potential in the measuring cell.

Figure 4:
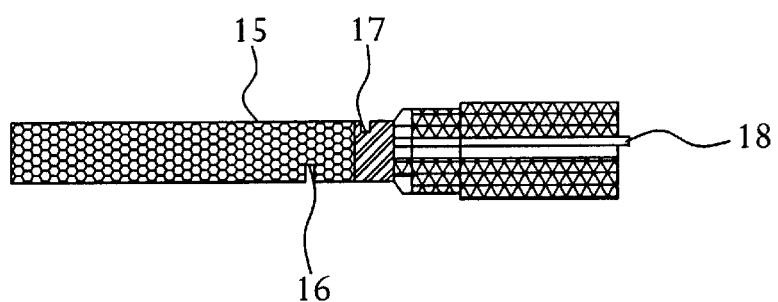
FIG. 4 is a schematic cross-sectional view of a linear functional element used in accordance with the hydrogen electrode of FIG. 3.

In FIG. 4 the linear functional element consists of a linear half-cell which is formed from an IEM strip (16) and an electrical chemically connected electrode strip (17). Both are embedded in a casting resin and are plugged onto the hydrogen tube with heat-shrinkable tubing (15). The numeral (18) illustrates the "broken" hydrogen tube with contact wire which conducts the electrode potential to the measurement terminal.

During production the heat-shrinkable tubing is pulled onto the tube end, coated with epoxy resin, and the linear half-cell element also coated with epoxy resin is inserted. The tubing is shrunk in a hot-air blower and the resin is simultaneously cured. By this elegant method numerous combinations of IEMs and electrodes can be produced as linear functional elements and mounted on electrochemical measuring devices with screw or plug adapters.

Figure 5:
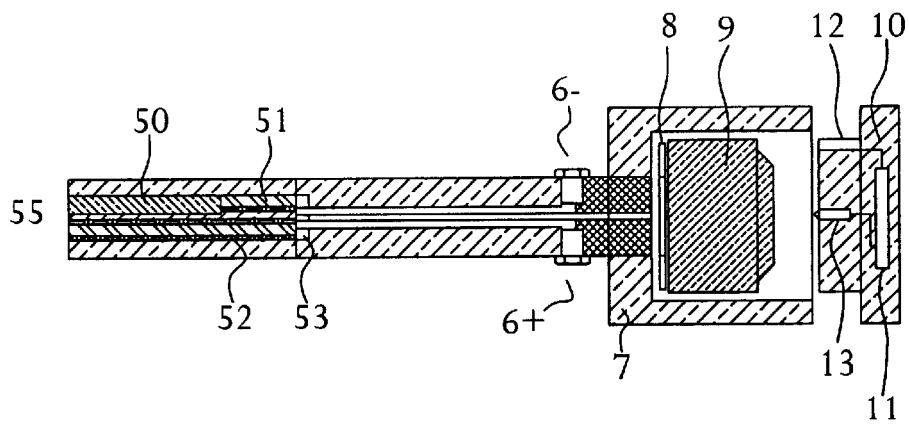
FIG. 5 is a schematic cross-sectional view of another embodiment of a hydrogen electrode of the invention.

In FIG. 5 a new type of device is shown which can be realized with the aid of the linear functional elements described here. It consists of three linear electrochemical elements (50), (51) and (52) in a hydrogen tube. The IEM (50) forms with the hydrogen electrode (51) a linear half-cell which is supplied with hydrogen in the space (53) from the gas evolution device. From the space (53) the hydrogen electrode (52) also gets its gas, hydrogen electrode (51) is connected to the contact screw 6+, hydrogen electrode (51) with the contact screw 6−. Upon immersion of the tip of the device (55) into an electrolyte solution one measures on the terminals (6+, 6−) a voltage reflecting the pH of the solution relative to that of the IEM (50). If a current is flowing in the measurement electrolyte then in front of (55) additionally a potential gradient prevails which is superimposed on the measurement. The component of this field which is present parallel to the end face (55) and which delivers a corresponding contribution to the voltage (6+, 6−) reverses this voltage contribution upon rotation of the device by 180°. In this way the fraction of impressed and reactive voltage in (6+, 6−) may be identified.

The common supply of the two hydrogen electrodes from one source eliminates the effects of hydrogen pressure and hydrogen temperature which are the same for both. It certainly does not take much imagination to conceive that in a gas tube instead of the one half-cell combination (50, 51) there are many of them, which are characterized by different IEMs, i.e. by different pH values. The corresponding linear functional elements may be arranged in the manner of a turret around a hydrogen electrode. They may open at the height of the terminals (6+) and (6−) in a circle of contacts on which a voltage can be measured in each case in pairs. As a result the possibility also exists of adaptation of the measurement standard to the pH of the object solution.

The dimensions of the linear elements which are stated above at 2 mm width, 1.5 mm thickness and any length, correspond to the frequently desired technical requirements. However, they also correspond to the adaptation to simple measuring instruments with conventional internal resistance. Interesting applications, however, arise through miniaturization in the case of medical applications since a regulated hydrogen source is also smaller than or may also be smaller than a swallowable tablet. The linear functional elements described here recognize no lower size limits.

The invention finds a simple application in determining and indicating the state of charge in lead batteries. Since the sulfuric acid of a battery cell is a part of the active mass and is bound as lead sulfate upon discharging, its concentration very precisely reports the charge that can still be drawn. In modern battery engineering, however, use is increasingly being made of systems in which the electrolyte is present in the form of a gel or in fleece-like separators. Then the acid accessible outside of the set of plates correlates only poorly with the actual state of charge. This invention of the linear functional elements enables us to insert one end into the set of plates between a positive $PbO_2$ electrode and a negative Pb electrode. This may be both the IEM strip as well as a hydrogen-diffusion electrode strip. In the case of the IEM strip the latter may as an electrochemical key form the connection with any reference electrode, preferably a hydrogen rod electrode as in FIG. 3. In the case of the hydrogen electrode the arrangement shown in FIG. 4 has proven effective. The voltage between the negative lead electrode of the battery cell and the reference electrode may be read out directly in units of the quantity of charge still available with consideration of the construction data of the battery cell.

What is claimed is:

1. A linear electrochemical functional element comprising a strip-shaped ion-exchange membrane (IEM) accessible at its ends and which is enclosed on all sides by a jacket of a solid insulating material.

2. A linear electrochemical functional element comprising a strip-shaped hydrogen-diffusion electrode accessible at its ends and which is enclosed on all sides by a jacket of a solid insulating material.

3. A linear electrochemical functional element comprising a half-cell accessible at its ends formed from an ion-exchange membrane and a hydrogen-diffusion electrode, and which is enclosed on all sides by a jacket of a solid insulating material.

4. The linear electrochemical functional element as in one of claims 1, 2 or 3, wherein the jacket is a metal with a passivated surface.

5. The linear electrochemical functional element as in one of claims 1, 2 or 3, wherein the jacket is a synthetic casting resin.

6. The linear electrochemical functional element as in claims 1, 2 or 3 wherein the functional element strip is connected to a hydrogen source.

7. An electrochemical cell for measuring pH and/or concentration of a solution in an electrochemical object with an electrode as a half-cell and a reference electrode in the form of a hydrogen rod electrode with an integrated hydrogen source comprising a linear electrochemical functional element as in claims 1, 2 or 3.

8. A lead battery cell comprising the electrochemical cell as in claim 7.

9. The lead battery cell as in claim 8, wherein the half-cell is a lead electrode and the lead electrode and the hydrogen rod electrode produce a voltage that is converted and read out as the charge state value of the lead battery cell.

* * * * *